(12) United States Patent
Kaplitt et al.

(10) Patent No.: US 8,021,838 B2
(45) Date of Patent: Sep. 20, 2011

(54) TRANSCRIPTIONAL REGULATION OF TARGET GENES

(75) Inventors: Michael G. Kaplitt, New York, NY (US); Matthew J. During, Philadelphia, PA (US); Andres M. Lozano, Toronto (CA)

(73) Assignees: The Rockefeller University, New York, NY (US); Thomas Jefferson University, Philadelphia, PA (US); Neurologix Research, Inc., Fort Lee, NJ (US)

( * ) Notice: Subject to any disclaimer, the term of this patent is extended or adjusted under 35 U.S.C. 154(b) by 525 days.

(21) Appl. No.: 11/542,651

(22) Filed: Oct. 3, 2006

(65) Prior Publication Data

US 2007/0059290 A1 Mar. 15, 2007

Related U.S. Application Data

(62) Division of application No. 10/151,702, filed on May 20, 2002, now abandoned.

(60) Provisional application No. 60/292,604, filed on May 21, 2001.

(51) Int. Cl.
*C12Q 1/68* (2006.01)
(52) U.S. Cl. .................. 435/6; 435/173.1; 536/24.1
(58) Field of Classification Search .................. None
See application file for complete search history.

(56) References Cited

U.S. PATENT DOCUMENTS

| | | | |
|---|---|---|---|
| 4,839,343 A | 6/1989 | Waeber et al. | |
| 4,892,105 A | 1/1990 | Prass | |
| 5,026,685 A | 6/1991 | Boublik et al. | |
| 5,219,740 A | 6/1993 | Miller et al. | |
| 5,385,915 A | 1/1995 | Buxbaum et al. | |
| 5,681,744 A * | 10/1997 | Greenstein | 435/320.1 |
| 5,981,225 A | 11/1999 | Kochanek et al. | |
| 6,071,889 A | 6/2000 | Weiss et al. | |
| 6,161,048 A | 12/2000 | Sluijter et al. | |
| 6,303,116 B1 | 10/2001 | Dornburg | |
| 2002/0099025 A1 * | 7/2002 | Heywood | 514/44 |

OTHER PUBLICATIONS

Morelli et al., J. Gen. Virol., (1999) vol. 80, pp. 571-583.*
Fujiki et al., Brain Res. Mol. Brain Res., 44:301-308 (2000).
Hausmann et al., Brain Res. Mol. Brain Res., 76:355-62 (2000).
Muller et al., Neuropsychopharm., 2:205-15 (2000).
Pelham, Cell, 30:517-528 (1982).
Rampon et al., Proc. Natl. Sci. U.S.A., 97:12880-12884 (2000).
Young et al., Nat. Med., 5:448-53 (1999).
Minth et al., The Journal of Biological Chemistry, 261:11974-11979 (1986).
Schmidt et al., "Transcriptional Control of the Mouse alpha2(I) Collagen Gene: Functional Deletion Analysis of the Promoter and Evidence for Cell-Specific Expression", Molecular and Cellular Biology, vol. 6, No. 2: 347-354, 1986.
Kreidberg et al., "Genetic Analysis of the Human Thymidine Kinase Gene Promoter", Molecular and Cellular Biology, vol. 6, No. 8: 2903-2909, 1986.
Chang et al., "Rat Gene Encoding the 78-kDa Glucose-Regulated Protein GRP78: Its Regulatory Sequences and the Effect of Protein Glycosylation on Its Expression", Proc. Natl. Acad. Sci. USA, vol. 84: 680-684, 1987.
Stougaard et al., "5' Analysis of the Soybean Leghaemoglobin lbc3 Gene: Regulatory Elements Required for Promoter Activity and Organ Specificity", The EMBO Journal, vol. 6, No. 12: 3565-3569, 1987.
Kaplitt et al., Preproenkephalin promoter yields region-specific and long-term expression in adult brain after direct in vivo gene transfer via a defective herpes simplex viral vector, Proc. Natl. Acad. Sci., vol. 91:8979-8983 (1994).
Scott et al., Gene transfer and in vivo promoter analysis of the rat progesterone receptor using a herpes simplex virus viral vector, Molecular Brain Research 114:91-100 (2003).
Jin et al., Prolonged in Vivo Gene Expression Driven by a Tyrosine Hydroxylase Promoter in a Defective Herpes Simplex Virus Amplicon Vector, Human Gene Therapy 7:2015-2024 (1996).
Lin et al., Regulating Genes with Electromagnetic Response Elements, Journal of Cellular Biochemistry 81:143-148 (2001).
Zhuo et al., Live Astrocytes Visualized by Green Fluorescent Protein in Transgenic Mice, Developmental Biology 187:36-42 (1997).

* cited by examiner

*Primary Examiner* — James S Ketter
(74) *Attorney, Agent, or Firm* — Klauber & Jackson LLC (57) ABSTRACT

The present invention describes a method of identifying inducible genetic regulatory sequences that can control the transcription of specific gene transcripts. Methods of using inducible genetic regulatory sequences are also discussed. In particular, the genetic regulatory sequences of the present invention can modulate the transcription of a nucleic acid transcript in vivo.

9 Claims, 4 Drawing Sheets

Figure 4 ive effects

SEQUENCE LISTING

```
<160> NUMBER OF SEQ ID NOS: 1

<210> SEQ ID NO 1
<211> LENGTH: 9
<212> TYPE: PRT
<213> ORGANISM: Artificial Sequence
<220> FEATURE:
<223> OTHER INFORMATION: Synthetic peptide

<400> SEQUENCE: 1

His Ser Glu Gly Thr Phe Thr Ser Asp
 1               5
```

TRANSCRIPTIONAL REGULATION OF TARGET GENES

CROSS REFERENCE TO RELATED APPLICATIONS

The present application is a Divisional Application of U.S. application Ser. No. 10/151,702 filed May 20, 2002, now abandoned which in turn claims priority under 35 USC §119 (e) to USSN provisional patent application 60/292,604 filed May 21, 2001. The disclosure of each of the above-identified applications is incorporated herein by reference in its entirety.

FIELD OF THE INVENTION

The present invention discloses a method of providing transcriptional control of specific gene transcripts. One particular use for such transcriptional control is in gene therapy. Specific genetic regulatory sequences, signaling devices, and peptides that emulate transcription factors, as well as the methods of using the same are also provided.

BACKGROUND OF THE INVENTION

During the past decade researchers have begun to lay a solid foundation for performing gene therapy related procedures. For example, long-term expression of heterologous genes in mammals was demonstrated using viral vectors engineered to contain tissue specific promoters (U.S. Pat. No. 6,040,172, herein specifically incorporated by reference in its entirety). In addition, a modification of behavior was demonstrated in an animal model for human Parkinson's Disease (U.S. Pat. No. 6,180,613, herein specifically incorporated by reference in its entirety). However, before gene therapy becomes a general medical practice, other factors must be addressed. One such factor concerns the regulation of the expression of the genetic transcript and/or the resulting gene product.

For example, many gene therapy strategies involve the expression of genes which are likely to cause adverse effects if they are expressed continuously. Thus, administering a gene transcript that is incapable of being regulated will oftentimes be unacceptable. In such cases, performing gene therapy with a regulatable gene expression system is necessary to control the expression of the otherwise therapeutic gene and/or gene product. Presently, regulatable promoters such as the metallothionein promoter, the tetracycline-on, and the tetracycline-off promoters are available. Unfortunately, such promoters are not well-suited for gene therapy because they are controlled by inducer compounds that are either toxic or can become toxic with long-term use. Still others are not practical for specific in vivo applications, e.g., they cannot cross the blood-brain barrier. Generally, the regulatable promoters that are currently employed in gene therapy strategies have been identified/selected for very different purposes and have therefore not been optimized for the particular role they must play in gene therapy.

Therefore, there is a need for developing methods for identifying genetic regulatory sequences (e.g., a promoter) that will be responsive to a stimulus in a particular tissue. In addition, there is a need for identifying stimulants of such genetic regulatory sequences that are both non-toxic and can readily gain access to the target tissue. There is a need for developing vectors that employ such genetic regulatory sequences for use in gene therapy. Further, there is a need to provide methods of performing gene therapy which employ the novel stimulants and genetic regulatory sequences of the present invention.

SUMMARY OF THE INVENTION

The present invention provides specific genetic regulatory sequences that can be controlled by specific stimulants in order to regulate the expression of exogenous genes in vivo. The present invention further provides methods for selecting such genetic regulatory sequences. In one embodiment the genetic regulatory sequence responds to a stimulus in a particular place and/or at a particular time. Thus, such a genetic regulatory sequence may be induced in a particular tissue and/or by the administration of a particular stimulus. For any given gene therapy strategy the type of tissue and stimulant is preferably pre-determined prior to its application.

In one embodiment, the genetic regulatory sequence responds to a pulsatile electromagnetic signal (e.g., stimulation). In a particular embodiment, the pulsatile signal can be turned on and off for at least 1 minute at a pulse frequency of 1 to 1000 hertz. In a specific embodiment, the pulse frequency is 10 to 400 hertz. In a more specific embodiment, the pulse frequency is 20 to 200 hertz. In an even more specific embodiment, the pulse frequency is 30 to 150 hertz. In one embodiment, the current is between 1 microamp and 50 milliamps. In a more specific embodiment, the current is between 10 microamps and 5 milliamps. In one embodiment, the voltage intensity is between 1 millivolt and 30 volts. In a more specific embodiment, the voltage intensity is between 100 millivolts and 10 volts.

In one embodiment, the individual pulse is 1 microsecond to 10 seconds. In a specific embodiment, the pulse is 20 microseconds to 1 second. In a more specific embodiment, the pulse width is 50 microseconds to 0.5 second. In an even more specific embodiment, the pulse width is 90 to 180 microseconds.

Thus, in one aspect of the present invention methods are provided for identifying a genetic regulatory sequence that is responsive to a pulsatile electromagnetic stimulus. One such method comprises inserting a stimulator into a tissue of an animal subject and applying a pulsatile signal with the stimulator in which at least a part of the tissue is stimulated. A gene is then identified that has either enhanced or diminished transcription in the part of the tissue stimulated, and a genetic regulatory sequence involved in the enhanced or diminished transcription of the gene is selected. This genetic regulatory sequence is thus identified as being responsive to the pulsatile electromagnetic stimulus. In a particular embodiment, the pulsatile electromagnetic signal is provided by a bipolar stimulator. In a related embodiment the pulsatile electromagnetic signal is provided by a monopolar stimulator.

In a particular embodiment, at least a part of the tissue is not stimulated by the signal of the stimulator and identifying a gene that has either enhanced or diminished transcription in the part of the tissue stimulated is performed by comparing the transcription of the genes in the part of the tissue stimulated with that of a part of the tissue that is not stimulated. In another embodiment, a second stimulator is placed into the part of the tissue that is not stimulated. In a specific embodiment of this type, no pulsatile signal is applied by the second stimulator. In an alternative embodiment, the entire tissue is stimulated.

In one embodiment of the invention, the tissue is neural tissue. In a specific embodiment, the neural tissue is brain tissue. In other embodiments, the tissue is heart tissue, liver tissue, or pancreatic tissue. In a particular embodiment of this embodiment, the pancreatic tissue contains the insulin producing beta cells from the islets of Langerhans.

In one embodiment, the pulsatile electromagnetic signal is magnetic. In a particular embodiment of this type the pulsatile electromagnetic signal is a transcranial magnetic stimulation. In another embodiment, the pulsatile electromagnetic signal is electrical.

In a second aspect, the invention features an isolated genetic regulatory sequence that has been identified by performing a method of the present invention. In one embodiment, the genetic regulatory sequence is responsive to a pulsatile electromagnetic signal. In a particular embodiment the pulsatile electromagnetic signal that the genetic regulatory sequence is responsive to is magnetic. In an alternative embodiment, the pulsatile electromagnetic signal that the genetic regulatory sequence is responsive to is electrical. In a related embodiment, the genetic regulatory sequence is responsive to a specific peptide identified by a method of the present invention.

The present invention further provides a vector for the in vivo expression of a gene of interest in a mammalian host cell which contains a gene of interest operatively under control of a genetic regulatory sequence identified by a method of the present invention. In a particular embodiment, the vector comprises a gene of interest operatively linked to a transcriptional control region comprising a genetic regulatory sequence that is responsive to a pulsatile electromagnetic stimulus. In one embodiment, the pulsatile electromagnetic signal is magnetic. In another embodiment, the pulsatile electromagnetic signal is electrical. In a particular embodiment, the genetic regulatory sequence of the transcriptional control region of the vector exhibits tissue specificity. In a specific embodiment, the genetic regulatory sequence of the transcriptional control region of the vector is obtained from a gene encoding a protein expressed by the cell which is selected to be the target cell for the vector.

In one embodiment, the vector is a replication defective viral vector. In a particular embodiment of this type, the vector is a replication defective herpes simplex virus (HSV). In another embodiment, the vector is a replication defective papillomavirus. In yet another embodiment, the vector is a replication defective Epstein Barr virus (EBV). In still another embodiment, the vector is a replication defective adenovirus and/or gutless adenovirus. In yet another embodiment, the vector is a replication defective adeno-associated virus(AAV). In still another embodiment, the vector is a replication defective lentivirus. In yet another embodiment, the vector is a replication defective retrovirus. In a particular embodiment of this type, the replication defective retrovirus vector is prepared for use in an ex vivo gene therapy protocol.

In one embodiment, the genetic regulatory sequence of the transcriptional control region of the vector is obtained from neural tissue. In a more specific embodiment of this type, the neural tissue is brain tissue. In other specific embodiment, the genetic regulatory sequence is obtained from heart tissue, liver tissue, or pancreatic tissue. In a particular embodiment of this type, the pancreatic tissue contains the insulin producing beta cells from the islets of Langerhans.

In a second aspect, the invention provides a non-human mammalian host transformed with a vector of the present invention. Preferably the expression of the gene of interest encoded by the vector can be modulated by applying a pulsatile electromagnetic signal with a stimulator. In a particular embodiment the pulsatile electromagnetic signal is magnetic. In an alternative embodiment the pulsatile electromagnetic signal is electrical. In a preferred embodiment, the stimulator is also present in the non-human mammalian host.

In a third aspect, the invention features methods of delivering the vectors of the present invention to a target tissue of an animal subject by administering the vector to the target tissue of the animal subject. Preferably the expression of the gene of interest encoded by the vector can be modulated by applying a pulsatile electromagnetic signal with a stimulator. In one embodiment, the pulsatile electromagnetic signal is magnetic. In an alternative embodiment, the pulsatile electromagnetic signal is electrical. In a particular embodiment, the transcription of the gene of interest in the target tissue is stimulated by the electromagnetic signal. In an alternative embodiment, the transcription of the gene of interest in the target tissue is hindered and/or inhibited by the electromagnetic signal. In a particular embodiment, the pulsatile electromagnetic signal is provided by a bipolar stimulator. In a related embodiment, the pulsatile electromagnetic signal is provided by a monopolar stimulator.

In a fourth aspect, the invention features methods of identifying a genetic regulatory sequence that is responsive to a peptide. One such method comprises contacting a peptide with a cell and identifying a gene that has either enhanced or diminished transcription. A genetic regulatory sequence involved in the enhanced or diminished transcription of the gene is selected. This genetic regulatory sequence is identified as being responsive to the peptide. In a preferred embodiment this peptide is a random generated peptide. In a particular embodiment, the peptide has the amino acid sequence of SEQ ID NO:1. In a more specific embodiment, the peptide is between 3 and 40 amino acids long. More specifically, the peptide is between 5 and 15 amino acids long. Randomly generated peptides that can either enhance or diminish transcription of the gene through binding to a genetic regulatory sequence are also included in the invention. Furthermore, genetic regulatory sequences that respond to these peptides are also part of the present invention, as are the vectors that comprise such genetic regulatory sequences.

In a fifth aspect, the invention features methods of regulating the expression of a gene of interest in a target tissue of an animal subject in which a vector of the present invention has been administered. One such method comprises applying a pulsatile signal with a stimulator to modulate the transcription of a gene of interest in the target tissue. In a particular embodiment of this aspect, the response to the pulsatile signal by the genetic regulatory sequence of the vector stimulates the transcription of the gene of interest in the target tissue. In an alternative embodiment, the response to the pulsatile signal by the genetic regulatory sequence reduces the transcription of the gene of interest in the target tissue. In a preferred embodiment of this type, the response to the pulsatile signal by the genetic regulatory sequence stops and/or prevents the transcription of the gene of interest in the target tissue.

In a sixth aspect, the invention features methods of ameliorating symptoms due to Parkinson's disease. One such method comprises administering glutamic acid decarboxylase to the subthalamic nucleus of a patient having a symptom of Parkinson's disease. In one such embodiment, the glutamic acid decarboxylase is administered to the subthalamic nucleus of the patient via a vector. In one particular embodiment, the vector is constructed to comprise a nucleic acid encoding glutamic acid decarboxylase operatively under the control of a genetic regulatory sequence that is stimulated by a pulsatile electromagnetic signal. A pulsatile electromagnetic signal is applied with a stimulator that had been placed into the subthalamic nucleus of the patient. The pulsatile electromagnetic signal stimulates the transcription of the glutamic acid decarboxylase in the subthalamic nucleus which leads to the amelioration of the symptom due to Parkinson's disease. In a preferred embodiment the vector is a replication defective viral vector. In a particular embodiment the vector comprises a chicken beta-actin promoter that is operatively linked to a nucleic acid encoding human glutamic acid decarboxylase (the CBA-GAD65 viral vector).

In a seventh aspect, the invention features a method of modulating the release of a stored compound by a cell. In a preferred embodiment the compound is a small organic molecule. In one such embodiment, the compound is a hormone and/or a neurotransmitter such as epinephrine, norepinephrine, dopamine, dopa, serotonin and GABA.

One embodiment of the method comprises administering to an animal subject (preferably a human) a vector comprising a nucleic acid encoding a protein (preferably an enzyme) operatively under the control of a genetic regulatory sequence. The genetic regulatory sequence is specifically chosen for its ability to be stimulated by a pulsatile electromagnetic signal, whereas the protein is specifically chosen for its ability, when expressed, to stimulate the production of a compound that is subsequently stored by a cell of the animal subject. A stimulator is then inserted into a tissue of the animal subject such that when it is used to apply a specific signal, the genetic regulatory sequence responds. In a particular embodiment exemplified below, the vector and the stimulator are administered to the subthalamic nucleus. A pulsatile electromagnetic signal is then applied with the stimulator, causing the protein to be expressed which thereby stimulates the production of the compound, which in turn is stored by a cell. At a subsequent time, a second pulsatile electromagnetic signal is applied with the stimulator which then modulates the release of the stored compound from the cell. In the Example 4 below, the compound is GABA. When the second pulsatile electromagnetic signal is performed at a low frequency, the cell is stimulated to increase the release of GABA, whereas when the second pulsatile electromagnetic signal is performed at a high frequency, the cell is stimulated to decrease (and/or block) the release of GABA.

Accordingly, the present invention provides genetic regulatory sequences that respond to pulsatile electromagnetic stimulation and are stimulated by pulsatile electromagnetic signals to facilitate the transcription of a nucleic acid operatively under their control. Further provided is a genetic regulatory sequence that responds to a pulsatile electromagnetic signal by hindering the transcription of a nucleic acid operatively under its control or by preventing the transcription of a nucleic acid operatively under its control.

The present invention also provides vectors and replication defective vectors that contain nucleic acids that are operatively under the control of a genetic regulatory sequence identified by a method of the present invention.

Further, the invention provides a method of modulating the transcription of a selected nuclei acid in vivo, including turning off transcription, by placing it operatively under the control of a genetic regulatory sequence identified by a method of the present invention.

Further, the present invention provides a method of performing gene therapy with a defective viral vector comprising a therapeutic nucleic acid that is operatively under the control of a genetic regulatory sequence of the present invention.

BRIEF DESCRIPTION OF THE DRAWINGS

FIG. 1 shows that in normal rats there is a large increase in impulse activity due to subthalamic nucleus stimulation. FIG. 2 shows an inhibition of spontaneous firing of the neuron in the substantia nigra due to subthalamic nucleus stimulation.

(i) 10 Hz, at 500 µA for 2 minutes, (labeled ST1); and
(ii) 10 Hz, at 500 µA for 5 minutes (labeled ST2).

DETAILED DESCRIPTION OF THE INVENTION

The present invention provides methods for controlling the transcription of heterologous genes in vivo by employing specific genetic regulatory sequences that can be up and/or down regulated, and preferably turned off and/or on by specific stimulators. Further provided are specific expression cassettes that include genes of interest operably under the control these genetic regulatory sequences, and methods of delivering these expression cassettes to the target cells. The methods of delivery include using standard transgenic techniques such as transfection and transduction. The expression cassettes can be included in both viral and non-viral vectors. The genetic regulatory sequences can be characterized based on screening gene expression patterns in a particular tissue following a defined stimulus. In a particular embodiment, the delivery of the expression cassette is to the nervous system and the genetic regulatory sequences are selected for their ability to be regulated in the nervous system.

The invention features a method for identifying genetic regulatory sequences for controlling expression of genes for gene therapy which respond to a physiological stimulus. In one such embodiment, a physiological stimulus is administered, and messenger RNA is extracted from the cells or tissue. Microarray analysis (see e.g., U.S. Pat. No. 6,215,894 and U.S. Pat. No. 6,004,755 herein specifically incorporated by reference in their entirety) can then be performed to identify genes having increased expression in response to the physiological stimulus. The genetic regulatory sequences from these genes can then be identified and/or isolated (e.g., by PCR or genomic library screening). The genetic regulatory sequences can then be inserted into expression cassettes to control the expression of a gene of interest. The physiological stimulus can then be used to control the expression of the gene of interest.

Methods other than microarray analysis may include, but are not limited to, differential display (see e.g., U.S. Pat. No. 6,045,998 and U.S. Pat. No. 5,599,672, herein specifically incorporated by reference in their entirety), subtractive mRNA hybridization (see e.g., U.S. Pat. No. 5,958,738 and U.S. Pat. No. 5,525,471, herein specifically incorporated by reference in their entirety), peptide arrays, two-dimensional protein gel electrophoresis and microsequencing of relevant peptides.

Stimuli may include, but are not limited to, electrical stimulation, magnetic fields, heat or cold stimuli, peptide or protein infusion, chemical or drug infusion, ionizing radiation, microwave or ultrasound.

A genetic regulatory sequence (e.g., a promoter or genetic response sequence/element) can be selected based upon the response of an endogenous cellular gene in a target tissue to a particular stimulus. Once identified, the genetic regulatory sequence can then be inserted into a gene therapy vector to control expression of any gene of interest in that target tissue.

The mammalian nervous system responds to environmental conditions including housing and enrichment paradigms (Young et al. (1999) Nat. Med. 5:448-53 and Rampon et al. (2000) Proc. Natl. Acad. Sci. U.S.A. 97:12880-12884), transcranial magnetic stimulation (Fujiki et al. (1997) Brain Res. Mol. Brain Res. 44:301-308; Muller et al. (2000) Neuropsychopharm. 2:205-15; and Hausmann et al. (2000) Brain Res. Mol. Brain Res. 76:355-62) and peripheral administration of exogenous compounds and peptides by inducing transcription of specific genes.

The expression of a number of proteins have been found to be responsive to high frequency TMS in rats, including glial acidic fibrillary protein (GFAP) expression (Fujiki et al. (1997) supra), c-fos, brain-derived neurotropic factor (BDNF) and cholecystokinin (CCK) (Muller et al. (2000) supra, and Hausmann et al. (2000) supra). The genetic regulatory equences of these genes may be employed in expression cassettes by the method of the present invention.

One particular aspect of the present invention is the use of essentially any peptide e.g., preferably 3 to 40 amino acid residues, and more preferably 5 to 15 amino acid residues, to selectively up and/or down regulate, and preferably turn on and/or turn off specific genes. Therefore, the present invention provides methods of identifying/mapping genes that are up and/or down regulated, and preferably turned on and/or off by any given peptide.

In particular, in Example 3 below, genes encoding the NMDA receptor, F3 contactin, and MAP-2 are shown to be upregulated in response to a novel peptide. Therefore, genetic regulatory sequences from the 5' promoter region of these genes are provided as a component of the gene switch. Initially, the isolated promoters can be cloned upstream of a marker gene such as green fluorescent protein (see e.g., U.S. Pat. No. 5,625,048, WO 97/26333, and WO 99/64592, herein specifically incorporated by reference in their entirety) or luciferase, which can then be used to further characterize the responsiveness to the peripheral administration of the peptide. Subsequently, important neural proteins (e.g., tyrosine hydroxylase, DARP-32 etc.) can be inserted in place of the marker proteins for gene therapy, for example.

Similarly, synthetic promoter constructs including multiple genetic regulatory sequences from the genes encoding CRE, p53, AP-1, SRE, NF-kappaB, SRF, Spl (using e.g., 3 to 10 copies of the response element) can be initially placed upstream of a luciferase and GFP cDNA. These expression cassettes can be cloned into an AAV cis plasmid and used to generate rAAV-RE (generic response element)-luc/GFP, for example. One such expression vector, the rAAV-Cre-luc has already been packaged and successfully injected into a group of rats. The present invention further provides "cocktails" of response elements which can be used to generate synthetic response elements that can either upregulate a given transgene or downregulate the transgene, depending on the stimulus applied.

Vectors may include, but are not limited to, adenovirus (recombinant and "gutless" vectors), herpes simplex virus (recombinant vectors and amplicons), adeno-associated virus, lentivirus, retrovirus, synthetic or non-viral vectors (including liposome and plasmid-based systems). Preferably the viral vectors are reproduction defective viral vectors.

It should also be noted that chimeric promoters or genetic response elements which contain some part of an endogenous promoter identified to be responsive to an external stimulus are also part of the present invention.

Definitions

As used herein, the term "gene" refers to an assembly of nucleotides that encodes a polypeptide and includes cDNA and genomic DNA nucleic acids. A gene is a nucleic acid that does not necessarily correspond to the naturally occurring gene which contains all of the introns and regulatory sequences, e.g., promoters, present in the natural genomic DNA. Rather, a gene encoding a particular protein can minimally contain just the corresponding coding sequence for the protein.

As used herein a "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase.

As used herein transcriptional and translational control sequences are DNA regulatory sequences, such as promoters, enhancers, terminators, and the like, that provide for the expression of a coding sequence in a host cell. In eukaryotic cells, polyadenylation signals are control sequences.

An "expression control sequence" is a DNA sequence that controls and regulates the transcription and translation of another DNA sequence. A coding sequence is "operatively under the control" of transcriptional and translational control sequences in a cell when RNA polymerase transcribes the coding sequence into a precursor RNA, which is then transRNA spliced to yield mRNA and translated into the protein encoded by the coding sequence.

A nucleotide sequence is "operatively under the control" of a genetic regulatory sequence when the genetic regulatory sequence controls and/or regulates the transcription of that nucleotide sequence. That genetic regulatory sequence can also be referred to as being "operatively linked" to that nucleotide sequence.

As used herein, a "genetic regulatory sequence" is a nucleic acid that: (a) acts in cis to control and/or regulate the transcription of a nucleotide sequence, and (b) can be acted upon in trans by a regulatory stimulus to promote and/or inhibit the transcription of the nucleotide sequence. Therefore, an inducible promoter is a genetic regulatory sequence. In addition, a portion of a promoter (e.g., fragment/element) that retains and/or possesses the ability to control and/or regulate the transcription of a nucleotide sequence either alone or in conjunction with an alternative promoter or fragment thereof (e.g., a chimeric promoter) is also a genetic regulatory sequence. Such fragments include response elements (genetic response elements) and promoter elements.

As used herein, an "expression cassette" is a nucleic acid that minimally comprises a nucleotide sequence to be transcribed (e.g., a coding sequence) that is operatively under the control of a genetic regulatory sequence.

A "signal sequence" can be included before the coding sequence. This sequence encodes a signal peptide, N-terminal to the polypeptide, that communicates to the host cell to direct the polypeptide to the cell surface or secrete the polypeptide into the media, and this signal peptide is clipped off by the host cell before the protein leaves the cell. Signal sequences can be found associated with a variety of proteins native to prokaryotes and eukaryotes.

As used herein, a "defective viral vector", abbreviated "dvv" is a viral vector that requires the expression and/or transcription of at least one nucleic acid that it lacks in order to be replicated and/or packaged. Preferably the dvv is a replication defective viral vector.

As used herein, a "heterologous gene" is a gene that has been placed into a vector or cell that does not naturally occur in that vector or cell.

As used herein, a gene is an "exogenous gene" when the gene is not encoded by the particular vector or cell.

A "vector" as used herein is a genetic construct that facilitates the efficient transfer of a nucleic acid (e.g., a gene) to a cell. The use of a vector can also facilitate the transcription and/or expression of that nucleic acid in that cell. Examples of vectors include plasmids, phages, amplicons, viruses and cosmids, to which another DNA segment may be attached so as to bring about the replication of the attached segment.

As used herein, "pulsatile" stimulation is a stimulation in which more than one pulse per unit time (and preferably a series of pulses) is generated at a defined pulse width. The number of pulses per unit time is termed its frequency which can be denoted in Hertz.

As used herein, a "pulse width" is the length of time a single pulse lasts.

As used herein, a "small organic molecule" is an organic compound, or organic compound complexed with an inorganic compound (e.g., metal) that has a molecular weight of less than 3 kilodaltons, and preferably less than 1.5 kilodaltons.

Gene Therapy

The genetic regulatory sequences of the present invention can be used to modulate gene transcription in any cell, including human cells. However, the genetic regulatory sequences of the present invention can be used to modulate gene transcription in cells of other mammals, such as rodents, e.g., mice, rats, rabbits, hamsters and guinea pigs; farm animals e.g., sheep, goats, pigs, horses and cows; domestic pets such as cats and dogs, higher primates such as monkeys, and the great apes such baboons, chimpanzees and gorillas.

The genetic regulatory sequences of the present invention can be operatively linked to any heterologous nucleic acid of interest, preferably those encoding proteins. Indeed, any protein can be encoded by the heterologous nucleic acid operatively under the control of a genetic regulatory sequence of the present invention. A short list of a few of these proteins and their roles in particular conditions and/diseases is included in Table 3 below. However, this listing should in no way limit the general methodology of the present invention which provides the ability to modulate the expression of any nucleic acid of choice. In addition, the expression cassettes of the present invention can be constructed to comprise multiple nucleic acids each encoding a different protein and all under the control of the same genetic regulatory sequence. Alternatively, different nucleic acids can be placed under the control of different genetic regulatory sequences. For example, the use of two genetic regulatory sequences, one of which stimulates transcription when treated with a pulsatile electromagnetic signal and the other which hinders transcription under the same conditions can be used to control the expression of two different genes at the same time by operatively linking one coding sequence to one genetic regulatory sequence and the other coding sequence to the other genetic regulatory sequence. For example, insulin and glucagon expression could be controlled in this manner. Alternatively, multiple expression cassettes can be employed encoding multiple different proteins.

TABLE 3

| Genetic Defects | Disease/Symptom |
|---|---|
| adenosine deaminase | severe combined immunodeficiency disease |
| alpha, - antitrypsin | pulmonary emphysema |
| 5-alpha reductase | male pseudohemaphroditism |
| 17 - alpha reductase | male pseudohemaphroditism |
| p53 or ARF-P19 | proteins linked to cancer |
| insulin | insulin-dependent diabetes |
| sickle cell anemia | B-globin |
| hypoxanthine guanine phosphoribosyl-transferase | Lesh-Nyhan Syndrone |
| ornithine transcarbamolase | Fatal to newborn males |
| phenylalanine hydroxylase | Phenylketonuria |
| Dralassemia | x- or B-globin |
| AT Page 7 A | Menkes' syndrome |
| AT Page 7B | Wilson Disease |
| hexosamindase A | Tay-Sachs Disease |
| acid cholesterylester hydrolase | Wolmon Disease |

In one particular example a defective viral vector comprising a nucleic acid encoding insulin operatively under the control of a genetic regulatory sequence of the present invention can be employed to transduce the pancreas in vivo to treat insulin-dependent diabetes. For example, if the genetic regulatory sequence is induced to stimulate transcription when a pulsatile electromagnetic signal is provided by a stimulator, expression of insulin could be controlled and the insulin-dependent diabetes treated. The vectors of the present invention can be delivered in vitro, ex vivo and in vivo.

When the genetic regulatory sequence is contained in a viral vector, the delivery can be performed by stereotaxic injection into the brain for example, as previously exemplified (U.S. Pat. No. 6,180,613, herein specifically incorporated by reference in its entirety); or via a guide catheter (U.S. Pat. No. 6,162,796, herein specifically incorporated by reference in its entirety) to an artery to treat the heart. In addition, the vectors of the present invention may also be delivered intravenously, intracerebroventricularly and/or intrathecally, for specific applications. Additional routes of administration can be local application of the vector under direct visualization, e.g. superficial cortical application, or other non-stereotactic applications.

For targeting a vector to a particular type of cell, it may be necessary to associate the vector with a homing agent that binds specifically to a surface receptor of the cell. Thus, the vector may be conjugated to a ligand (e.g., enkephalin) for which certain nervous system cells have receptors, or a surface specific antibody. The conjugation may be covalent, e.g., a crosslinking agent such as glutaraldehyde, or noncovalent, e.g., the binding of an avidinated ligand to a biotinylated vector.

In addition, the helper-free defective viral vectors of the present invention can be delivered ex vivo, as exemplified by Anderson et al. (U.S. Pat. No. 5,399,346, herein specifically incorporated by reference in its entirety).

Alternatively, a vector can be introduced by lipofection. Liposomes can be used for encapsulation and transfection of nucleic acids. Synthetic cationic lipids designed to limit the difficulties and dangers encountered with liposome mediated transfection can be used to prepare liposomes for in vivo transfection of a gene encoding a marker (Feigner et al. (1987) Proc. Natl. Acad. Sci. USA 84:7413-7417; see also Mackey et al. (1988), Proc. Natl. Acad. Sci. U.S.A 85:8027-8031). The use of cationic lipids may promote encapsulation of negatively charged nucleic acids, and also promote fusion with negatively charged cell membranes (Feigner et al. (1989) Science 337:387-388). The use of lipofection to introduce exogenous genes into the specific organs in vivo has certain practical advantages. Molecular targeting of liposomes to specific cells represents one area of benefit. It is clear that directing transfection to particular cell types would be particularly advantageous in a tissue with cellular heterogeneity, such as pancreas, liver, kidney, and the brain. Lipids may be chemically coupled to other molecules for the purpose of targeting (Mackey et. al. (1988) supra).

It is also possible to introduce the vector as a naked DNA plasmid. Naked DNA vectors for gene therapy can be introduced into the desired host cells by methods known in the art, e.g., transfection, electroporation, microinjection, transduction, cell fusion, DEAE dextran, calcium phosphate precipitation, use of a gene gun, or use of a DNA vector transporter (see, e.g., Wu et al. (1992) J. Biol. Chem. 267:963-967; Wu et al. (1988) J. Biol. Chem. 263:14621-14624; Hartmut et al., Canadian Patent Application No. 2,012,311, filed Mar. 15, 1990).

In an ex vivo method of the invention, the genetic regulatory sequences of the invention are delivered to a host cell to be transplanted into a mammalian recipient. The host cells may be endogenous or exogenous to the mammalian recipient. The term "transplant cell" refers broadly to the component, e.g., tissue or cells, being grafted, implanted, or transplanted into a recipient subject. As used herein, the term "transplantation" refers to the transfer or grafting of tissues or cells from one part of a subject to another part of the same subject or to another subject. Transplanted tissue may comprise a collection of cells of identical composition, or derived from a donor organism, or from an in vitro culture. Delivery of the genetic regulatory sequences of the invention to a transplant cell may be accomplished by any of the methods known to the art and described above, e.g., as a plasmid, as part of a vector; by injection, lipofection, etc.

A variety of dissociated cells can be implanted, using standard techniques for isolation and transplantation of tissue or organs, such as livers. See, for example, U.S. Pat. Nos. 6,281, 015, herein specifically incorporated by reference.

Transgenic Animals

A transgenic animal model can be prepared so as to contain a nucleic acid operatively under the control of a genetic regulatory sequence of the present invention. For example transgenic vectors, including viral vectors, or cosmid clones (or phage clones) can be constructed. Cosmids may be introduced into transgenic mice using published procedures (Jaenisch (1988) Science 240:1468-1474).

Thus the present invention further provides transgenic, knock-in, and knockout animals that contain one or more heterologous genes operatively under the control of a genetic regulatory sequence of the present invention. These animals can be used as animal models in drug screening assays. In one such example, a drug can be added under various "controlled" expression levels of a particular gene, or at various time points before and/or after induced expression of the particular gene, allowing a much more detailed investigation of the effects of that drug on a particular condition. In a specific embodiment, the transgenic, knock-in, or knockout animal is a mouse. Cells from the inducible knockout, knock-in and/or transgenic animals of the present invention are also part of the present invention. These cells can also be used in the drug assays, for example.

Transgenic animals can be obtained through gene therapy techniques described above or by microinjection of a nucleic acid for example, into an embryonic stem cell or an animal zygote (such as a bacterial artificial chromosome (BAC) comprising a nucleic acid operatively under the control of a genetic regulatory sequence of the present invention). Microinjection of BACs has been shown to be successful in a number of animals including rats, rabbits, pigs, goats, sheep, and cows (in Transgenic Animals Generation and Use (1997) ed., L. M. Houdebine, Harwood Academic Publishers, The Netherlands). Methods of constructing BACs or other DNAs such as bacteriophage P1 derived artificial chromosomes (PACs) that encode specific nucleic acids through homologous recombination have recently been described in great detail (Heintz et al. (1998) PCT/US98/12966, herein specifically incorporated by reference in its entirety). Alternatively, a yeast artificial chromosome (YAC) can be used.

Ribozymes and Antisense

Antisense nucleic acids are DNA or RNA molecules that are complementary to at least a portion of a specific mRNA molecule (see Weintraub (1990) Sci. Amer. 262:40-46; Marcus-Sekura (1987) Nucl. Acid Res, 15:5749-5763; Marcus-Sekura (1988) Anal. Biochem. 172:289-295); Brysch et al. (1994) Cell Mol. Neurobiol. 14:557-568). Preferably, the antisense molecule employed is complementary to a substantial portion of the mRNA. In the cell, the antisense molecule hybridizes to that mRNA, forming a double stranded molecule. The cell does not translate an mRNA in this double-stranded form. Therefore, antisense nucleic acids interfere with the expression of mRNA into protein. Preferably a DNA antisense nucleic acid is employed since such an RNA/DNA duplex is a preferred substrate for RNase H.

Oligomers of greater than about fifteen nucleotides and molecules that hybridize to the AUG initiation codon will be particularly efficient. Antisense methods have been used to inhibit the expression of many genes in vitro (Marcus-Sekura (1988) supra; Hambor et al. (1988) Proc. Natl. Acad. Sci. U.S.A. 85:4010-4014) and in situ (Arima et al. (1998) Antisense Nucl. Acid Drug Dev. 8:319-327; Hou et al. (1998) Antisense Nucl. Acid Drug Dev. 8:295-308).

Ribozymes are RNA molecules possessing the ability to specifically cleave other single stranded RNA molecules in a manner somewhat analogous to DNA restriction endonucleases. Ribozymes were discovered from the observation that certain mRNAs have the ability to excise their own introns. By modifying the nucleotide sequence of these ribozymes, researchers have been able to engineer molecules that recognize specific nucleotide sequences in an RNA molecule and cleave it (Cech (1988) JAMA 260:3030-3034; Cech (1989) Biochem. Intl. 18:7-14). Because they are sequence-specific, only mRNAs with particular sequences are inactivated.

Investigators have identified two types of ribozymes, Tetrahymena-type and "hammerhead"-type (Haselhoff et al. (1988) Nature 334:585-591). Tetrahymena-type ribozymes recognize four-base sequences, while "hammerhead"-type recognize eleven- to eighteen-base sequences. The longer the recognition sequence, the more likely it is to occur exclusively in the target mRNA species. Therefore, hammerhead-type ribozymes are preferable to Tetrahymena-type ribozymes for inactivating a specific mRNA species, and eighteen base recognition sequences are preferable to shorter recognition sequences.

Antisense nucleic acids and/or ribozyme can also be placed operatively under the control of a genetic regulatory sequence of the present invention. Such an expression cassette, when placed in vector (e.g., a viral vector) and appropriately administered can be used to selectively modulate the expression of a particular protein in a cell, tissue or animal subject. This procedure would be complementary to modulating the transcription of the gene encoding the protein described above, since in this case the gene would be transcribed but selectively prevented from being expressed. For example, the administration of an antisense nucleic acid or ribozyme that prevents the over-expression of tumor necrosis factor alpha, which arises in septic shock, leprosy or tuberculosis, by the methodology disclosed herein may be particularly beneficial.

Specific Embodiments

The present invention may be better understood by reference to the following non-limiting Examples, which are provided as exemplary of the invention. The following examples are presented in order to more fully illustrate the preferred embodiments of the invention. They should in no way be construed, however, as limiting the broad scope of the invention.

One method for regulating the expression of a heterologous gene is to place it operatively under the control of an inducible promoter. Unfortunately, whereas promoter activity and gene expression differ fundamentally when examined in vitro relative to in vivo most of the inducible promoters currently being employed have been optimized to control gene expression in cultured cells, rather than in a living animal. For example, electrical stimulation of astroglial cells in tissue culture recently has been shown to induce expression of a marker gene under the control of the inducible hsp70 promoter (hsp 70) (Pelham (1982) Cell 30:517-528; Yanagida et al. (2000) J. Biotechnology 79:53-61). However, the hsp70 promoter responds non-specifically to a variety of stresses including chemical toxicity, heat stress, and ischemia and there was no direct evidence provided that the hsp 70 promoter was specifically responsive to the electrical stimulation applied. Moreover, whereas astroglial cells placed in tissue culture are required to divide, in their native state in the brain they normally do not undergo cell division. Therefore, it was not surprising to find that in vivo the hsp 70 promoter was not effected by electrical stimulation of the brain (Example 1).

Prior to the experiments described below, the use of electrical stimulation to control the expression of a heterologous protein in vivo has not been substantiated. Therefore, a nucleic acid encoding a heterologous protein (luciferase) was placed into an expression cassette under the control of a genetic regulatory sequence (i.e., a 2.2 kb 5' fragment of the human glial acidic fibrillary protein gene) that responds to electrical stimulation. The expression cassette, the recombinant viral vector, rAAV-GFAP-Luc, was then delivered (i.e., injected) to an animal subject. The electrical stimulation was applied and the luciferase activity was determined in resected hippocampi.

As described in Example 2, an electrical stimulator can be inserted into the brain to control expression of a heterologous gene contained in an expression vector (e.g., a viral vector). Whereas a variety of stimulators are currently used for nerve or brain stimulation to alter neuronal firing activity, they have never been used to control gene expression.

Example 3 describes the infusion of a peptide intranasally into rats, and subsequent changes in gene expression in a variety of brain regions were analyzed.

Parkinson's Disease is a neurodegenerative disorder characterized by loss of the nigrostriatal pathway and is responsive to treatments which facilitate dopaminergic transmission in the caudate-putamen (Yahr et al. (1987) *Parkinson's Disease* (Raven Press); Yahr et al. (1969) Arch. Neurol. 21:343-54). Unilateral 6-hydroxydopamine lesions of the substantia nigra have been used to generate an established rodent model of Parkinson's Disease.

Electrophysiology studies have demonstrated that the subthalamic nucleus (STN) has a prominent excitatory connection with the substantia nigra (SN). In Parkinson's disease (PD), the subthalamic nucleus is overactive and this overactivity may lead to progressive degeneration of dopamine neurons in the subthalamic nucleus as well as the common features of Parkinson's disease such as tremor, rigidity and bradykinesia. As described in Example 4 below, changing the excitatory projection from the subthalamic nucleus to the substantia nigra into an inhibitory projection alleviates the symptoms associated with Parkinson's disease.

EXAMPLES

Example 1

Use of Electrical Stimulation to Regulate Genes

Materials and Methods: Rats: Male-Sprague-Dawley, Fisher, Wistar and Lewis strains of rats were used for all experiments.

Transcranial Magnetic Stimulation: An adeno-associated viral (AAV) vector expressing the luciferase transgene under control of a genetic regulatory sequence from the human 2.2 kb glial acidic fibrillary protein (GFAP) promoter was injected stereotactically into the left dorsal hippocampus of young adult male rats. After four weeks, groups of rats were randomized to exposure to the 5 cm Cadwell coil without activating the stimulator (i.e., mock stimulation), to low frequency stimulation (5 Hz) or to high frequency (25 Hz) delivered as trans (30 trains, each 10 second duration). Stimulation or mock stimulation was given once daily for four days with the 5 cm coil centered over the left hippocampus. On day 5, rats were euthanized and hippocampi resected and analyzed for luciferase activity.

As shown in Table 1, the amount of luciferase activity measured correlated with the amount of electrical stimulation applied. As a further control, luciferase activity in a group of completely naive control rats was found to be undetectable after stimulation (<10 pg). As is apparent from Table 1, expression of luciferase that is operatively under the control of the GFAP promoter element increases with electrical stimulation (see methods). Therefore, the use of 5' elements or response elements isolated from the promoter regions of inducible genes can be used to generate similarly regulated transcription units.

TABLE 1

Effect of Electrical Stimulation on Luciferase Activity in The Hippocampi of Rats Injected with an rAAV-GFAP-Luc Vector.

| STIMULATION (Hz) | ACTIVITY (pg/hc)[a] | FOLD INCREASE |
| --- | --- | --- |
| mock | 109 ± 92[b] | 1 |
| 5 | 348 ± 178 | 2 |
| 2 | 1754 ± 326 | 16 |

[a]pg luciferase activity/hippocampus
[b](mean, S.D.)

Example 2

Selection of Genetic Regulatory Sequences to Regulate an Exogenous Gene

Bipolar stimulators were inserted bilaterally into the caudate nuclei of the rat. Stimulation was then performed on the left caudate for 30 minutes at high frequency (200 Hz) with a current of 200 μA, while a stimulator was inserted into the right caudate but remained off. Following the stimulation the animals were sacrificed, the right and left caudate nuclei were dissected and the tissue samples were rapidly frozen. mRNA was extracted from the tissues, and microarray analysis was performed comparing the mRNA from the left (stimulated) caudate nucleus to the right (unstimulated) caudate. This procedure was replicated in four animals.

Analysis of the data revealed significant changes in approximately 70 genes, with a high consensus among all samples and replicates. The majority of genes were turned off, with some genes decreasing in amount and eight genes were expressed in increasing amounts. Promoters were next isolated by PCR from four genes which were turned off (i.e., protein kinase B kinase, snyaptic vesicle protein 2B, phosphatidylinositol 3-kinase p85, and calcineurin B), and one gene, insulin-like growth factor-1 (IGF-1) that was increased in response to stimulation.

Next promoter fragments between 2.0 and 3.5 kb were inserted into adeno-associated virus (AAV) vectors containing the gene for green fluorescent protein (GFP). AAV vectors were then packaged and purified using standard techniques. In a specific example, the calcineurin B promoter/GFP construct was packaged and 3 µl of purified vector stocks were then infused bilaterally into the rat caudate nucleus in five animals. Brain stimulators were inserted bilaterally into the same point in the brain and were fixed to the skull with dental cement. After 48-72 hours of recovery, the left stimulator was turned on for 30 minutes at high frequency (200 Hz) with a current of 200 µA, while the right stimulator remained off. Animals were then sacrificed, and the tissue was harvested. Protein was extracted for western blot analysis that were performed using a monoclonal anti-GFP protein and standard techniques. The results showed that the GFP protein levels from the left (stimulated) caudate nucleus was decreased relative to that of the right (unstimulated) caudate.

The construct was then modified to encode tyrosine hydroxylase (TH) rather than green fluorescent protein. Previously the expression of tyrosine hydroxylase from viral vectors in the caudate nucleus of rat models of Parkinson's disease was shown to result in therapeutic improvement (U.S. Pat. No. 6,180,613, herein specifically incorporated by reference in its entirety).

In an analogous experiment, the construct encoding TH was also shown to be responsive to electronic stimulation (i.e., as described above for the corresponding GFP construct). In the case of the TH construct, a significant decrease in tyrosine hydroxylase mRNA levels from the left (stimulated) caudate nucleus relative to that of the right (unstimulated) caudate was determined by quantitative polymerase chain reaction (PCR) assays.

Example 3

Use of Peripherally Administered Peptides to Regulate Genes

Peripherally Administered Peptides: A novel peptide was synthesized that comprised nine amino acids having the amino acid sequence of HSEGTFTSD (SEQ ID NO:1). This peptide was administered intranasally at a dose of 30 µg to rats and was found to have no effect on spontaneous locomotor behavior, stereotype, feeding, nor did it influence pain threshold. Twenty minutes following the administration, the rats were sacrificed and their hippocampi removed. The hippocampi were subsequently dissected and the hippocampi RNA was isolated. The isolated RNA was then used for gene expression profiling using AFFYMETRIC rat gene chips (containing approximately 7000 cDNA's and EST's). Additional groups of rats received the vehicle control or amphetamine. Analysis of the gene expression data showed that in comparison to the vehicle treated rats, a large number of genes had expression that increased by greater than twenty fold. These genes included the neural adhesion molecule F3, bcl-w, MAP-2, NMDA Receptor, mGluR5 (another glutamate receptor) each of which increased by 20-70 fold at this twenty minute time point.

Example 4

Administrating a Viral Vector Encoding Glutamic Acid Decarboxylase into the Subthalamic Nucleus Electrophysiology and microdialysis were performed in the substantia nigra of normal rats and rats treated with a CBA-GAD65 viral vector encoding human glutamic acid decarboxylase (GAD65/67). Glutamic acid decarboxylase converts glutamate to GABA in neurons. The CBA-GAD viral vector was injected into the subthalamic nucleus three weeks before 6-OHDA lesions of the medial forebrain bundle. Electrophysiology and microdialysis were performed at least 4 months after the transduction of the viral vector.

Figure 1:
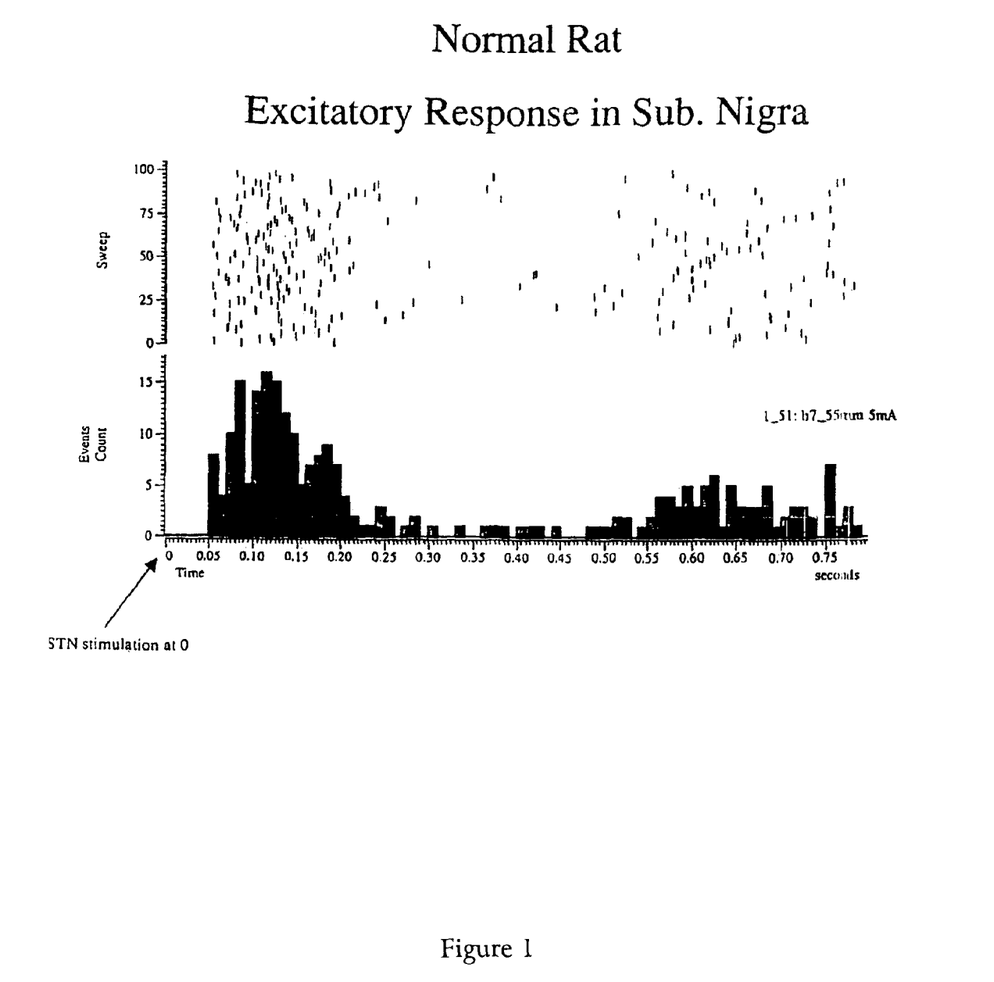
FIGS. 1-2 show the response of a neuron in the substantia nigra to electrical stimulation of the subthalamic nucleus. A histogram (20 ms bins) of spike counts after an electrical stimulation at t=0 is shown. Each trial of the stimulation is used to create the histogram and as a labeled sweep of the graph.
Figure 2:
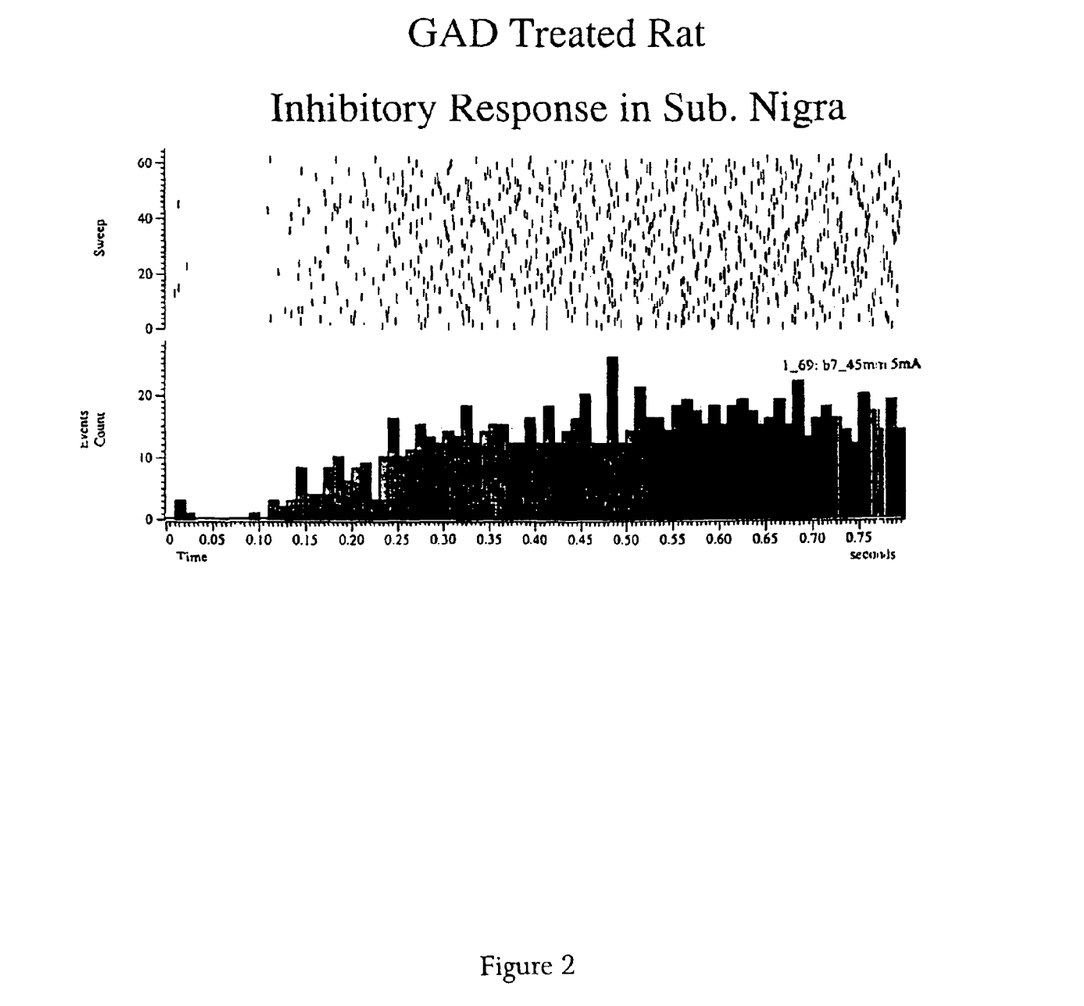
Figure 3:
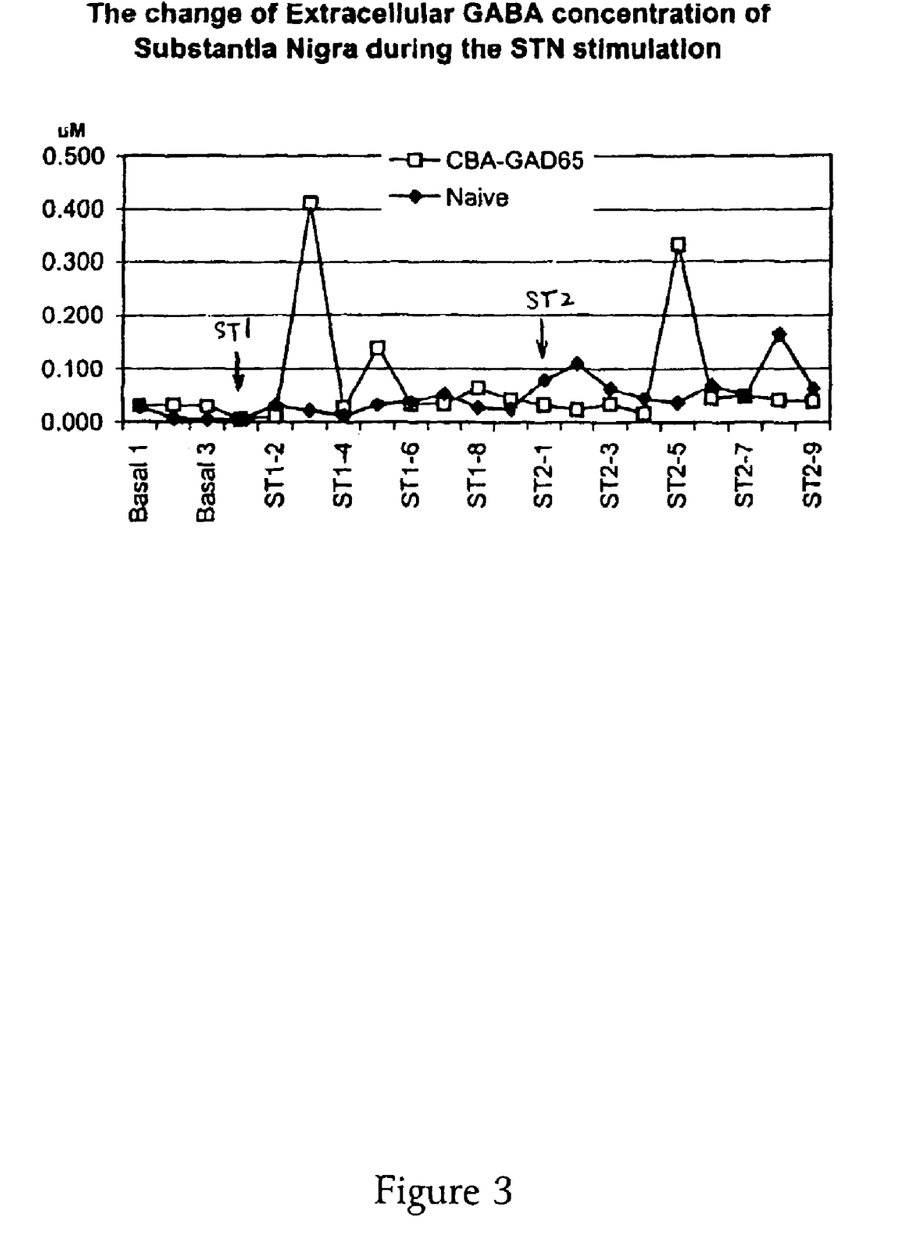
FIGS. 3-4 show the change of extracellular GABA concentration (FIG. 3) and glutamate concentration (FIG. 4) of the substantia nigra and the subthalamic nucleus during subthalamic nucleus stimulation in naive rats and rats transduced with a CBA-GAD65 viral vector. The stimulation was applied for two different time periods, two minutes and five minutes for two different groups of rats as shown.
Figure 4:
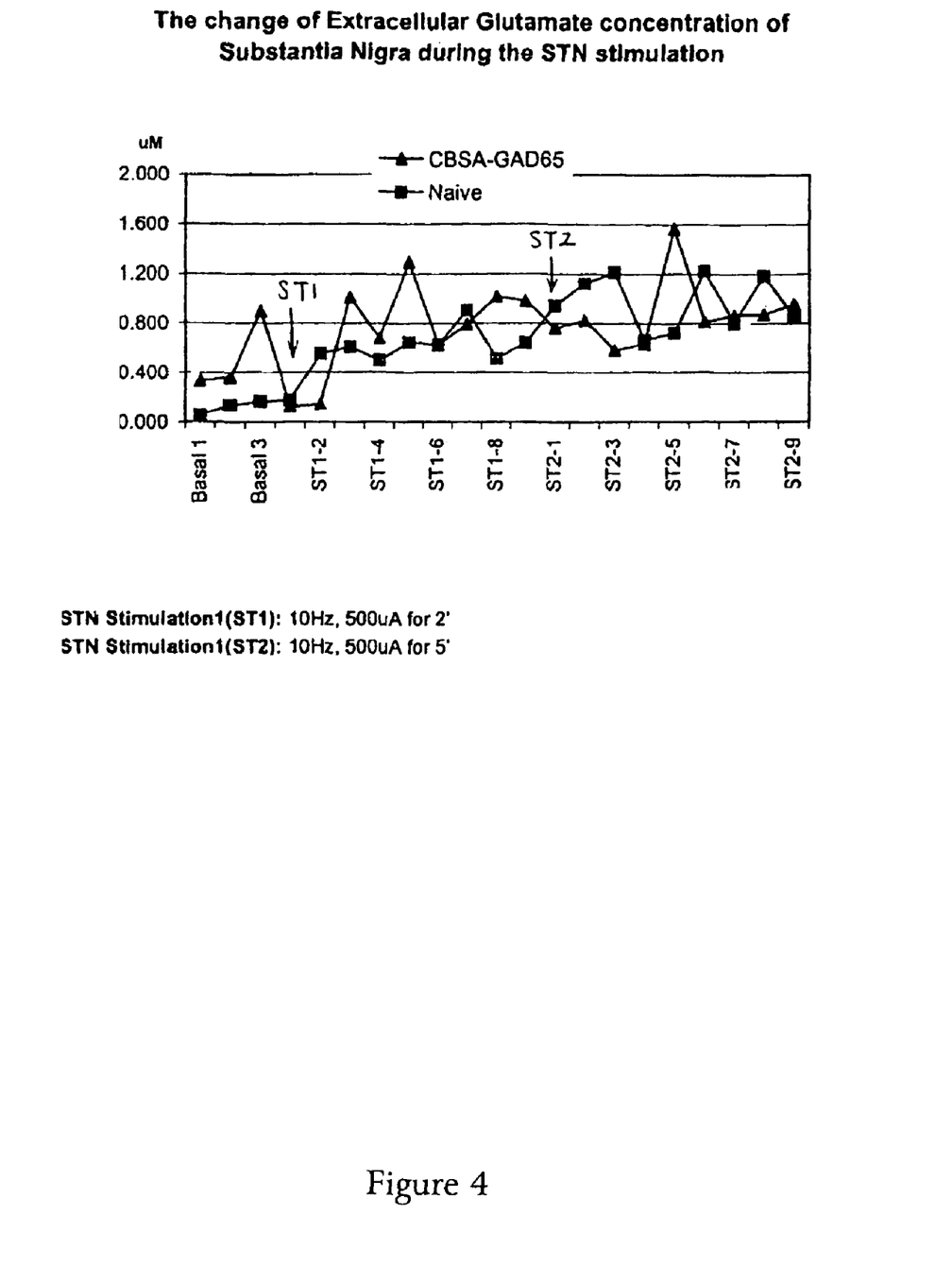

Inhibitory GABA containing connections were detected from the subthalamic nucleus to the substantia nigra using electrophysiology and microdialysis. In the microdialysis experiments a much higher (~10×) increase in GABA was detected due to low frequency electrical stimulation of the subthalamic nucleus, compared to the increase in naive control rats. Table 2 shows the extracellular concentration of GABA and glutamate in the substantia nigra obtained before and after low frequency stimulation in a rat transduced with the CBA-GAD viral vector as compared to a naive control rat. FIGS. 3 and 4 correspond to the data in Table 2. In contrast, high frequency stimulation blocked GABA release in the microdialysis experiment, demonstrating that the release of GABA, quite independent of transcriptional regulation, can be modulated by electromagnetic (e.g., electrical) stimulation.

TABLE 2

SUBSTANTIA NIGRA MICRODIALYSIS DURING THE SUBTHALAMIC NUCLEUS STIMULATION

| Sample 5 ul/15 ul | Flow Rate (1.0 ul/min) | GAD65 | | NAIVE | |
|---|---|---|---|---|---|
| | | GABA uM | GLU uM | GABA uM | GLU uM |
| Basal 1 | | 0.031 | 0.328 | 0.027 | 0.056 |
| Basal 2 | | 0.033 | 0.357 | 0.007 | 0.133 |
| Basal 3 | | 0.030 | 0.894 | 0.004 | 0.168 |
| ST1-1 LFS-1: 10 Hz, 500 uA for 2' | | 0.006 | 0.125 | 0.004 | 0.178 |
| ST1-2 | | 0.010 | 0.143 | 0.031 | 0.553 |
| ST1-3 | | 0.410 | 1.008 | 0.021 | 0.606 |
| ST1-4 | | 0.026 | 0.673 | 0.011 | 0.501 |
| ST1-5 | | 0.139 | 1.290 | 0.032 | 0.644 |
| ST1-6 | | 0.033 | 0.624 | 0.037 | 0.623 |
| ST1-7 | | 0.034 | 0.787 | 0.052 | 0.904 |
| ST1-8 | | 0.065 | 1.009 | 0.027 | 0.514 |
| ST1-9 | | 0.043 | 0.976 | 0.023 | 0.639 |
| ST2-1 LFS-2: 10 Hz, 500 uA for 5' | | 0.032 | 0.758 | 0.078 | 0.938 |
| ST2-2 | | 0.023 | 0.819 | 0.108 | 1.121 |
| ST2-3 | | 0.033 | 0.580 | 0.061 | 1.213 |
| ST2-4 | | 0.016 | 0.629 | 0.043 | 0.661 |
| ST2-5 | | 0.332 | 1.564 | 0.036 | 0.718 |
| ST2-6 | | 0.044 | 0.809 | 0.068 | 1.220 |
| ST2-7 | | 0.049 | 0.863 | 0.049 | 0.796 |
| ST2-8 | | 0.041 | 0.866 | 0.164 | 1.183 |
| ST2-9 | | 0.038 | 0.951 | 0.061 | 0.852 |

Note:
Each sample was collected every 5-6 minutes.

What is claimed is:

1. A method of identifying a genetic regulatory sequence responsive to a pulsatile electromagnetic stimulus, comprising:
   (a) inserting a stimulator into a tissue of an animal subject;
   (b) applying a pulsatile electromagnetic signal with the stimulator; wherein at least a part of the tissue is stimulated;
   (c) identifying a gene that has either enhanced or diminished transcription in the part of the tissue stimulated; and
   (d) selecting a genetic regulatory sequence involved in the enhanced or diminished transcription of the gene; wherein the genetic regulatory sequence is identified as being responsive to the pulsatile electromagnetic stimulus.

2. The method of claim 1, wherein the pulsatile electromagnetic signal is provided by a bipolar stimulator.

3. The method of claim 1, wherein the pulsatile electromagnetic signal is provided by a monopolar stimulator.

4. The method of claim 1, wherein at least a part of the tissue is not stimulated by the stimulator; and wherein the identifying of step (c) is performed by comparing the transcription of the genes in the part of the tissue stimulated with that of a part of the tissue that is not stimulated.

5. The method of claim 4, wherein a second stimulator is placed into the part of the tissue that is not stimulated; and wherein no pulsatile signal is applied by the second stimulator.

6. The method of claim 1, wherein the tissue is neural tissue.

7. The method of claim 6, wherein the neural tissue is brain tissue.

8. The method of claim 1, wherein the pulsatile electromagnetic signal is a magnetic stimulation.

9. A method of identifying a promoter fragment comprising a genetic regulatory sequence responsive to a pulsatile electromagnetic stimulus, comprising:
   (a) inserting a stimulator into a tissue of an animal subject;
   (b) applying a pulsatile electromagnetic signal with the stimulator; wherein at least a part of the tissue is stimulated;
   (c) analyzing expression of genes in the at least a part of the tissue to determine if transcription of any of the genes is either enhanced or diminished in the part of the tissue stimulated, whereby identifying a gene that has either enhanced or diminished transcription in the part of the tissue stimulated identifies a target gene; and
   (d) analyzing the target gene nucleic acid sequence to select the promoter fragment involved in the enhanced or diminished transcription of the target gene, wherein the promoter fragment is identified as responsive to the pulsatile electromagnetic stimulus.

* * * * *